(12) United States Patent
Ratcliffe et al.

(10) Patent No.: US 8,864,844 B2
(45) Date of Patent: Oct. 21, 2014

(54) TISSUE SCAFFOLD

(75) Inventors: Anthony Ratcliffe, Del Mar, CA (US); Andreas Kern, San Diego, CA (US); Fatemeh Ratcliffe, Del Mar, CA (US)

(73) Assignee: Synthasome, Inc., San Diego, CA (US)

( * ) Notice: Subject to any disclaimer, the term of this patent is extended or adjusted under 35 U.S.C. 154(b) by 917 days.

(21) Appl. No.: 11/890,989

(22) Filed: Aug. 9, 2007

(65) Prior Publication Data

US 2007/0276509 A1   Nov. 29, 2007

Related U.S. Application Data

(63) Continuation of application No. PCT/US2005/016393, filed on May 11, 2005.

(60) Provisional application No. 60/570,204, filed on May 11, 2004.

(51) Int. Cl.
| | | |
|---|---|---|
| *A61F 2/02* | (2006.01) | |
| *A61L 27/40* | (2006.01) | |
| *A61L 27/38* | (2006.01) | |
| *A61L 27/58* | (2006.01) | |
| *A61L 27/54* | (2006.01) | |
| *A61L 27/36* | (2006.01) | |

(52) U.S. Cl.
CPC ............ *A61L 27/38* (2013.01); *A61L 2300/406* (2013.01); *A61L 27/3633* (2013.01); *A61L 2300/414* (2013.01); *A61L 2300/602* (2013.01); *A61L 27/54* (2013.01); *A61L 27/58* (2013.01)
USPC ....................... 623/23.74; 623/23.75; 424/424

(58) Field of Classification Search
None
See application file for complete search history.

(56) References Cited

U.S. PATENT DOCUMENTS

| | | |
|---|---|---|
| 4,963,489 A | 10/1990 | Naughton et al. |
| 5,830,708 A | 11/1998 | Naughton |
| 5,916,585 A | 6/1999 | Cook et al. |
| 6,140,039 A | 10/2000 | Naughton et al. |
| 6,143,293 A | 11/2000 | Weiss et al. |
| 6,228,117 B1 * | 5/2001 | De Bruijn et al. ......... 623/16.11 |
| 6,284,284 B1 | 9/2001 | Naughton |
| 6,306,169 B1 | 10/2001 | Lee et al. |
| 6,319,712 B1 | 11/2001 | Meenen et al. |
| 6,451,060 B2 | 9/2002 | Masuda et al. |
| 2002/0120291 A1 * | 8/2002 | Shalaby ........................ 606/230 |
| 2003/0023316 A1 * | 1/2003 | Brown et al. .............. 623/23.72 |
| 2003/0203003 A1 * | 10/2003 | Nelson et al. ................. 424/426 |
| 2003/0208279 A1 | 11/2003 | Atala |
| 2004/0062753 A1 | 4/2004 | Rezania et al. |

FOREIGN PATENT DOCUMENTS

| | | |
|---|---|---|
| CA | 2 370 810 | 10/2000 |
| CA | 2 365 376 | 6/2002 |
| EP | 1 405 649 | 4/2004 |
| WO | WO 99/03979 | 1/1999 |
| WO | WO 01/03750 | 1/2001 |
| WO | WO 01/85226 | 11/2001 |
| WO | WO 0185226 A1 * | 11/2001 |

OTHER PUBLICATIONS

Ye et al. ASAIO Journal 2000 46:730-733.*
Supplementary European Search Report from EP 05 75 4269 Jul. 4, 2011.

* cited by examiner

*Primary Examiner* — Robert A Wax
*Assistant Examiner* — H. Sarah Park
(74) *Attorney, Agent, or Firm* — Carter, DeLuca, Farrell & Schmidt, LLP

(57) ABSTRACT

A tissue engineered construct made totally or in part from biocompatible materials and mammalian cells and/or cell products is provided. These constructs are useful in regenerating complex tissues such as bone, ligament and tendon, which may fabricated into medical devices suitable for use in the treatment of injuries and maladies such as rotator cuff injuries, periodontal disease and hernia.

20 Claims, 5 Drawing Sheets

Cell adhesion to Vicryl scaffold and scaffold-PLGA membrane composite. DNA of adhered cells was quantified after incubation at 37°C using the CyQuant kit. Composite constructs adhered approximately 30% more cells than scaffold alone at low and high cell densities.

TISSUE SCAFFOLD

RELATED APPLICATIONS

This application is a continuation of International Application PCT/US05/16393 filed May 11, 2005, which claims priority to U.S. Provisional Patent Application No. 60/570,204 filed May 11, 2004, the entire disclosure of each of which are incorporated herein in their entirety by this reference.

TECHNICAL FIELD

A structure useful as an implantable device made totally or in part from biocompatible materials and mammalian cells and/or mammalian cell products is provided.

BACKGROUND

Many complex tissues in the adult mammal fail to regenerate following injury or disease. For example, a critical sized defect in bone will fail to regenerate. Ligaments do not regenerate if destroyed by disease or injury such as the dental ligament in periodontal disease. Dermal ulcers in the elderly, diabetic, or individuals with venous stasis pathology can become chronic wounds that fail to heal. One approach to repair damage of this sort is referred to as Tissue Engineering wherein cells on matrices are used to affect tissue repair that would not occur without such an intervention. Tissue scaffolds are known in the art, see for example U.S. Pat. Nos. 6,451,060, 5,830,708, 6,284,284, 6,143,293, 6,306,169, 6,319,712, 6,228,117, and 5,916,585, and PCT and U.S. Patent Applications WO 99/03979, WO 01/03750, WO 01/85226, and US2003/0023316.

U.S. Pat. No. 4,963,489 discloses a living stromal tissue prepared in vitro, having stromal cells and connective tissue proteins naturally secreted by the stromal cells attached to and substantially enveloping a framework composed of a biocompatible, non-living material formed into a three dimensional structure having interstitial spaces bridged by the stromal cells.

U.S. Pat. No. 5,830,708 discloses the production of an extracellular matrix secreted by stromal cells onto a three dimensional substrate. The substrate is composed of a biocompatible, non-living material formed into a three-dimensional structure having interstitial spaces bridged by the stromal cells. The cells are removed to provide a cell free implant.

U.S. Pat. No. 6,140,039 discloses a three-dimensional filamentous tissue providing the function of a tendon or a ligament which has fibroblasts and collagen naturally secreted by the fibroblasts attached to and substantially enveloping a three-dimensional filamentous framework composed of a biocompatible, non-living material having interstitial spaces bridged by the fibroblasts.

However, such structures have limitations. The method of cell seeding is usually inefficient, as the cells must attach to the fibers, and the pores allow many of the cells to pass through the scaffold, resulting in inefficient cell seeding. The cells must fill the interstitial spaces by proliferation of the cells attached to the scaffold at the edge of the interstitial space, and must then deposit an extracellular matrix. This is a relatively slow process, and results in loss of synthesized and secreted matrix into the media, until the cells provide a confluent layer of cells across the interstitial space. This can result in an inconsistent manufacturing process. There is therefore a need to increase efficiency of the cell attachment and growth process, and deposition of the extracellular matrix.

Therefore, it would be advantageous to provide an improved scaffold system that results in increased efficiency of cell attachment, allowing cells to attach across large areas of the scaffold, rather than only at the edge of interstitial spaces. A scaffold that provides for larger number of cells to attach would result in more rapid formation of a confluent layer and more rapid matrix deposition compared to scaffolds wherein cells attach only to fibers and must grow to fill interstitial spaces.

SUMMARY

Provided is a tissue scaffold system that includes a scaffold fabricated from biocompatible materials that are enveloped in a biocompatible material providing a substrate for cell attachment. The scaffold consists of a three dimensional network fabricated from biocompatible mesh, non-woven felt, sponge or the like. Scaffold materials may be degradable or non-degradable. The scaffold is enveloped in a bioabsorbable material that is either porous or continuous. In some embodiments, the scaffold is embedded or encased in a bioabsorbable material. In other embodiments, one or more membranes are layered with or encase the scaffold. During manufacturing, cells will proliferate and deposit an extracellular matrix that condenses onto the underlying scaffold thus forming a three-dimensional tissue. The tissue construct may be further processed to eliminate living cells, but retain the extracellular matrix. The scaffold may be modified to provide desired characteristics, such as mechanical strength. Enveloping the fibrous scaffold in a biocompatible material allows cell attachment to occur across the complete area of the scaffold, resulting in high cell seeding density and increased cell seeding efficiency. The reduced permeability (compared to a scaffold that is not enveloped in a biocompatible material) results in increased matrix deposition. The final outcome will be increased efficiency of growth of a tissue engineered construct. Optionally, therapeutic agents, including growth factors such as VEGF or FGF4, cytokines, lipids, guidance factors, antimicrobial agents, and antibiotics are incorporated therein. The scaffold construct optionally includes an ionic charge, cell attachment ligands, or surface features such as ridges or grids to provide for oriented growth of cells.

BRIEF DESCRIPTION OF THE DRAWINGS

Various embodiments are described herein with reference to the drawing wherein.

DETAILED DESCRIPTION

It has now been found that a tissue scaffold system that includes a scaffold fabricated from biocompatible materials enveloped in a biocompatible material provides an improved substrate for cell attachment. In one embodiment, the biocompatible used to envelope the scaffold is bioabsorbable. During manufacture, cells will proliferate and deposit an extracellular matrix that condenses onto the underlying scaffold as the enveloping bioabsorbable material absorbs, thus forming a three-dimensional tissue.

Suitable scaffolds include meshes, other filamentous structures, non-woven, sponges, woven or non-woven materials, knit or non-knit materials, felts, salt eluted porous materials, molded porous materials, 3D-printing generated scaffolds, foams, perforated sheets, grids, parallel fibers with other fibers crossing at various degrees, and combinations thereof. The core scaffold can be in a variety of shapes including sheets, cylinders, tubes, spheres or beads. The core scaffold may be fabricated from absorbable or non-absorbable materials. Suitable absorbable materials include glycolide, lactide, trimethylene carbonate, dioxanone, caprolactone, alklene oxides, ortho esters, polymers and copolymers thereof, collagen, hyaluronic acids, alginates, and combinations thereof. Suitable non-absorbable materials include, polypropylene, polyethylene, polyamide, polyalkylene therephalate (such as polyethylene therephalate polybutylene therephalate), polyvinylidene fluoride, polytetrafluoroethylene and blends and copolymers thereof.

Figure 1:
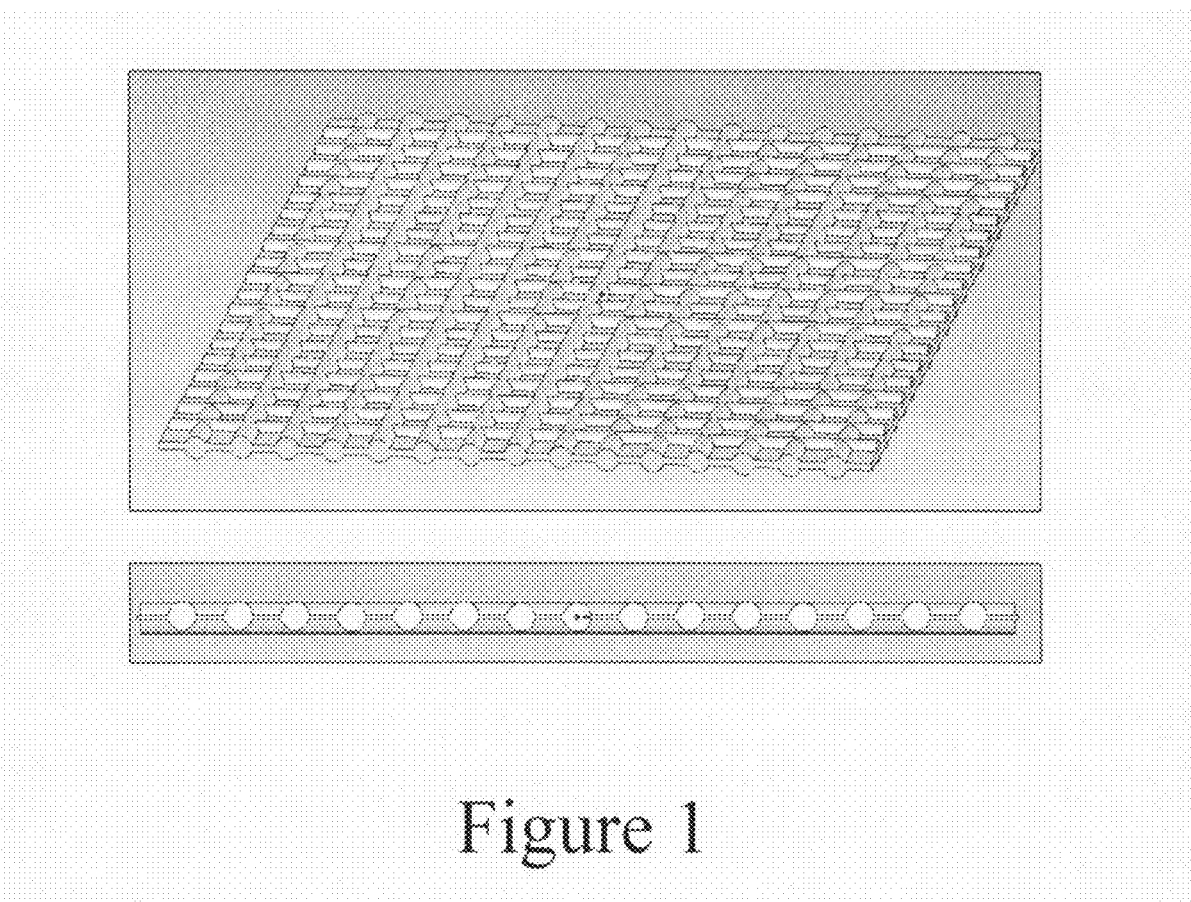
FIG. 1 is a schematic view of a scaffold system in accordance with one embodiment of this disclosure wherein a fibrous scaffold is embedded within a biocompatible material.
Figure 2:
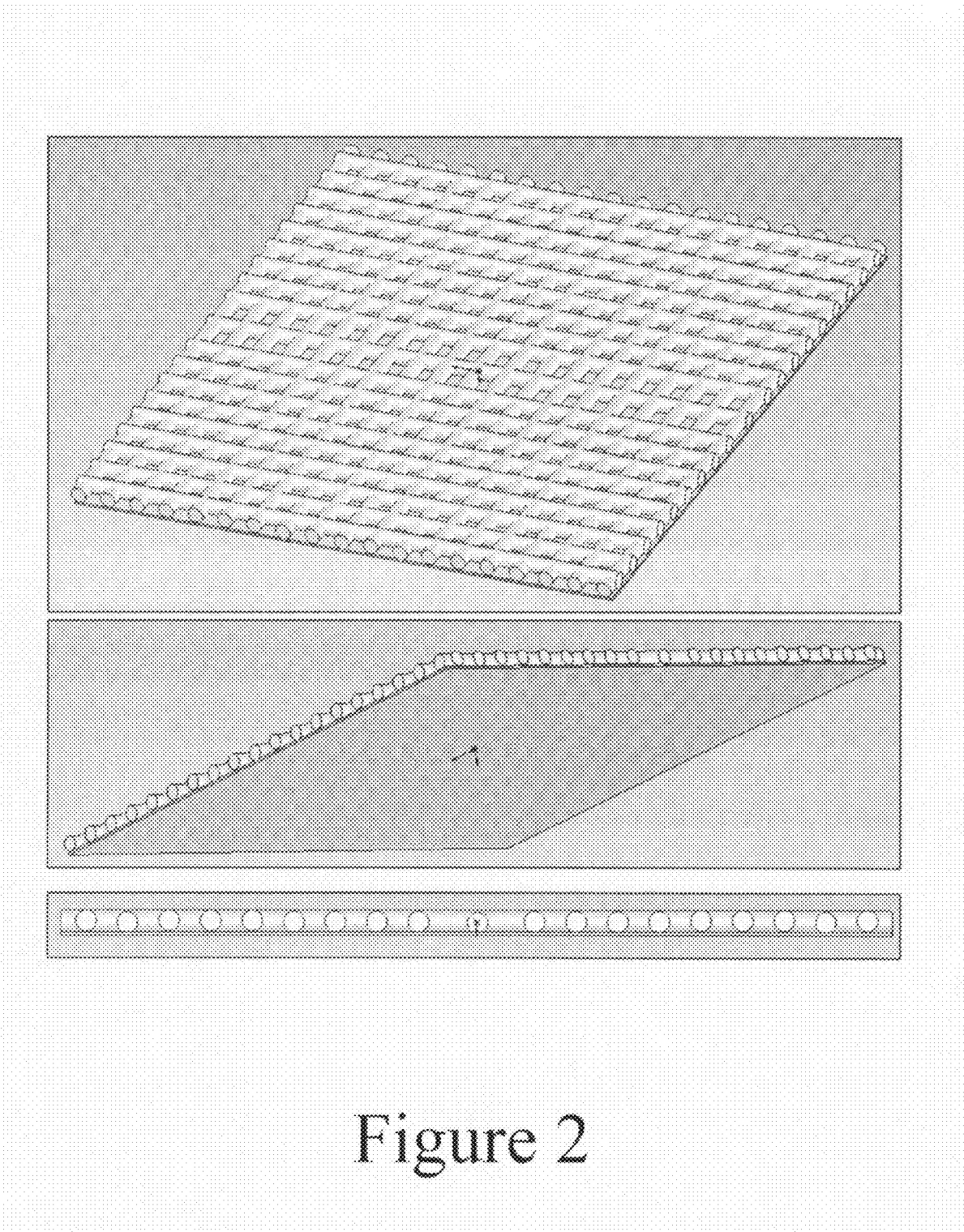
FIG. 2 is a schematic view of a scaffold system in accordance with another embodiment of this disclosure wherein a fibrous scaffold is used with a single membrane made from a biocompatible material.
Figure 3:
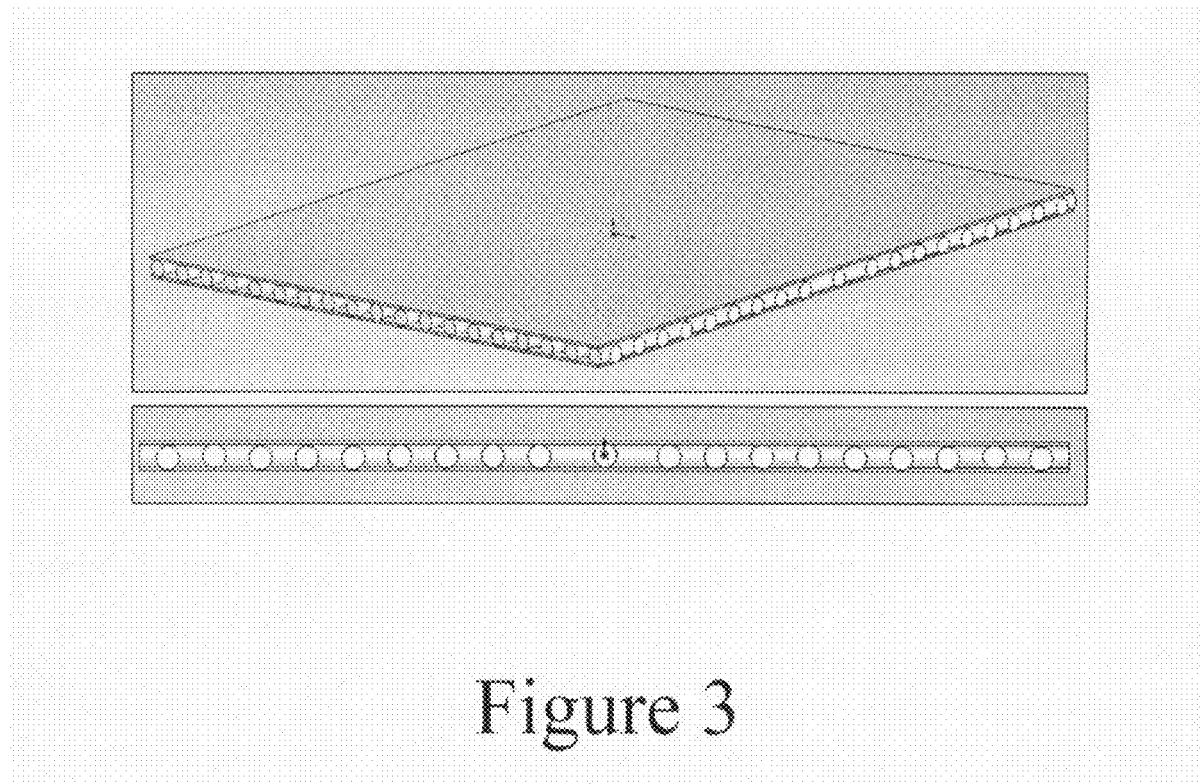
FIG. 3 is a schematic view of a scaffold system in accordance with yet another embodiment of this disclosure wherein a fibrous scaffold is enveloped between two biocompatible membranes.

Suitable biocompatible materials that can be used to envelope the scaffold include absorbable or non-absorbable materials or a combination thereof. Suitable absorbable materials include those stated hereinabove. Suitable non-absorbable materials include those non-absorbable materials stated hereinabove. In some embodiments, the scaffold is embedded or encased in a bioabsorbable material, see, FIG. 1. In these embodiments, the biocompatible material may be applied using techniques within the purview of those skilled in the art. Suitable techniques include, for example, dipping the scaffold into a solution of the biocompatible material. In other embodiments, one or more membranes are layered with or encase the scaffold. See, FIGS. 2 and 3. The scaffold may be secured to the one or more membranes or may float freely between the membranes in those embodiments where two membranes are used. Suitable techniques for securing the scaffold to the membrane(s) are within the purview of those skilled in the art. The biocompatible materials used to envelope the scaffold is either porous or non porous. Suitable pore sizes range from about <0.1 µm to about 10 µm. The biocompatible materials used to envelope the scaffold may be smooth or it may be engineered to have a surface texture. In one embodiment, the biocompatible material used to envelope the scaffold material is modified to have defined surface characteristics such as ridges or grids to promote directional deposition of extracellular matrix materials. In this embodiment, the matrix has orientation that may be advantageous for properties such as mechanical strength or flexibility in specific directions. In another embodiment, the biocompatible material used to envelope the scaffold is modified to include certain cell attachment ligands such as the RGD peptide. In a further embodiment, the outer surface of the biocompatible materials used to envelope the scaffold is modified to create a net positive or negative charge.

Where a bioabsorbable material is used to envelope the scaffold, the degradation rate can be adjusted by varying a number of parameters including, but not limited to composition, thickness, pore size and pore density. In some embodiments, the biocompatible materials used to envelope the scaffold will be 50% degraded within four to six weeks. Longer or shorter degradation times can, of course, be used.

The enveloped membrane structure is then seeded with cells that adhere to the outer membrane using conventional techniques, such as those described in (a) Earle et al., Production of Malignancy In Vitro; IV; The mouse fibroblast cultures and changes seen in the living cells, J. Natl. Cancer Inst. 4:165-212, 1943; (b) Schreiber R, Ratcliffe A. Tissue engineering of cartilage. In: Methods in Molecular Biology; Eds C Streuli and M Grant, Humana Press, pp 301-309, 2000; and (c) Kern A, Liu K, Mansbridge J. Modification of fibroblast gamma-interferon responses by extracellular matrix. J Invest Dermatol 2001 117: 112-118, the entire contents of which are incorporated herein by reference. The cells are cultured until a cell layer develops with a rich extracellular matrix, also using conventional techniques, such as those described in Alitalo et al., Extracellular matrix proteins characterize human tumor cell lines, Int J Cancer 27(6): 755-61, 1981, the contents of which are incorporated herein by reference. Suitable cells include but are not limited to fibroblasts, stromal cells, or stem cells. In an embodiment, the cells that are seeded on the scaffold have been selected to secrete an extracellular matrix similar to that of a specific tissue. For example, cartilage can be formed by seeding the scaffold system with chondrocytes. Similarly, tendons can be formed by seeding the scaffold system as the tendon fibroblasts. Dermis can be created by seeding normal dermal fibroblasts. In another embodiment, the cells are selected on the basis of the production of certain factors that will promote wound healing, regeneration or integration of the graft into the host. Such factors may include extracellular matrix molecules such as fibronectin and laminin or growth factors such as EGF, FGF, PDGF and VEGF. In another embodiment, the cells that are seeded on the scaffold have been genetically modified to secrete growth promoting factors. In another embodiment, the cells that are seeded on the scaffold have been genetically modified to express cell surface components such as human complement inhibitors to minimize the host immunological responses. The resultant engineered tissue may have biologic properties such as the ability to induce angiogenesis, promote wound healing, and/or prevent adhesions.

In an embodiment, the cells are extracted from the device providing a cell free device consisting of only the extracellular matrix components. This may be by freezing and thawing the device when the growth period is complete, to kill and fragment the cells, followed by a rinsing procedure to remove the majority of the cell fragments. Constructs containing cells, membranes or scaffolds will be grown until the appropriate proliferation and matrix production has been completed. Growth medium will be exchanged at regular intervals. At the end of the growth period, growth medium will be removed and replaced by physiologic salt solution and will be frozen in buffered saline solutions or growth medium in the absence of cryopreservatives (glycerol, DMSO, polyvinylpyrrolidone etc). This process will effectively kill off cells and remove soluble cellular components. Cellular components remaining may be removed using solutions containing detergents, including, but not limited to SDS, Triton etc., and/or solutions containing chaotropic agents including but not limited to Urea, Guanidinium chloride etc., and/or solutions containing high concentration of salt, including but not limited to sodium chloride. Alternatively, cells can be extracted using hypotonic salt solutions, leading to the terminal disruption of cells by osmotic pressure.

In a further embodiment, the cells are not extracted from the device.

In order that those skilled in the art may be better able to practice the compositions and methods described herein, the following examples are given as an illustration of the preparation of the tissue scaffold system. It should be noted that the invention is not limited to the specific details embodied in the examples and further that all ratios or parts recited are by weight, unless otherwise indicated.

EXAMPLE 1

A scaffold is made by knitting PLA fibers to provide an open porous structure, with pore sizes of approximately 500 µm. The scaffold is dipped in a gelatin solution, and allowed to dry so that a continuous collagen membrane forms over the PLA scaffold. The continuous collagen membrane is approximately 20 µm in thickness.

Cells are seeded as described previously (Kern et al., Schreiber et al., supra). Scaffolds and membranes are modified by incubation with cell attachment factors, including but not limited to fibronectin and its proteolytic fragments, collagen and its proteolytic or thermal fragments (gelatin), extracellular matrix proteins secreted by stromal cells in culture and their proteolytic or thermal fragments. Non-attached proteins or fragments are removed by washing with physiologic salt solutions, including saline or growth medium. Cells are removed from growth vessels using a physiologic salt solution containing Trypsin and EDTA and resuspended at concentrations ranging from $10^4$ to $10^7$ per milliliter growth medium in the presence or absence of serum. Cells are incubated with scaffolds or membranes for one to 18 hours at physiologic temperatures to allow for the firm attachment of the cells to the membrane or scaffold. Subsequently, fresh growth medium replaces the seeding solution and the cells attached to the membrane or scaffold are incubated at physiologic temperatures to allow for proliferation and matrix deposition.

EXAMPLE 2

A scaffold is made by knitting PLA fibers to provide an open porous structure, with pore sizes of approximately 500 µm. Membranes of approximately 20 µum in thickness are prepared from a 50:50 copolymer of polylactic acid and polyglycolic acid. The scaffold is laid onto the membrane and another layer of membrane is placed onto the top of the scaffold, providing a three layered material. The three layers are adhered together along one edge using a biocompatible adhesive. The cell seeding and culturing methods of Example 1 are then followed.

EXAMPLE 3

Figure 4:
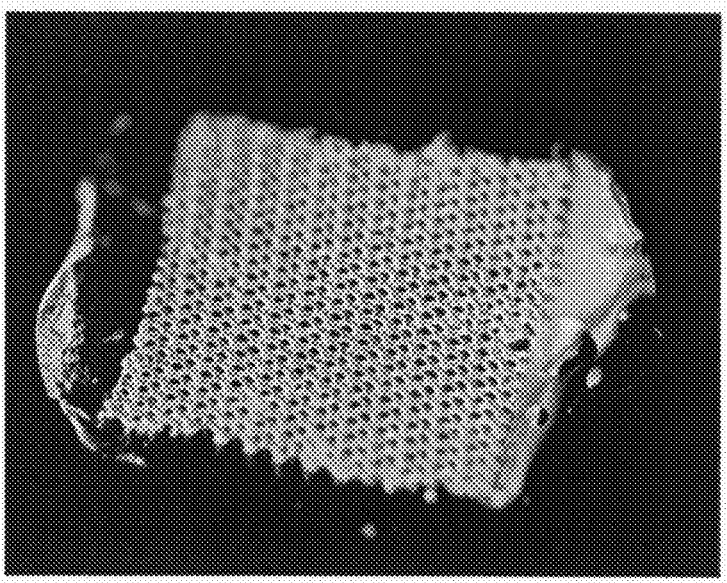
FIG. 4 shows a scaffold system in accordance with one embodiment of this disclosure wherein a knitted Vicryl® fibrous scaffold is embedded within a PGLA as the biocompatible material.

In a further in vitro illustrative of the method according to the present disclosure, dermal fibroblasts were seeded onto scaffold-membrane composites. A commercially available knitted material, Vicryl®, was used as the scaffold. Pursuant to the present methods, 2 grams of solid PLGA was dissolved in 20 ml of acetone and the scaffold submerged in the solution. The solvent was evaporated leaving the scaffold embedded in solid PLGA material. (See, FIG. 4). The scaffold-membrane composite was subsequently cut and stored under vacuum. Prior to seeding with cells, the composite was immersed in DMEM growth medium containing 10% bovine calf serum, non-essential amino acids, L-glutamine and Penicillin-Streptomycin antibiotics.

Human dermal fibroblasts were grown in tissue culture to passage 4 using the growth medium described above. Confluent cell cultures were harvested with Trypsin-EDTA solution, collected by centrifugation and resuspended in growth medium. After counting, approximately $1 \times 10^5$ cells or $3 \times 10^5$ cells were seeded onto the scaffold-membrane composite. The cultures were placed in tissue culture incubators (37° C., 5% $CO_2$) for four hours.

After the incubation period, non-attached cells were removed by repeated washing with PBS. Attached cells were quantified using the CyQuant DNA quantification kit from Molecular Probes, Inc., Eugene, Oreg. DNA was released from the cells using the lysis solution containing the fluorescent dye CyQuant GR.

Figure 5:
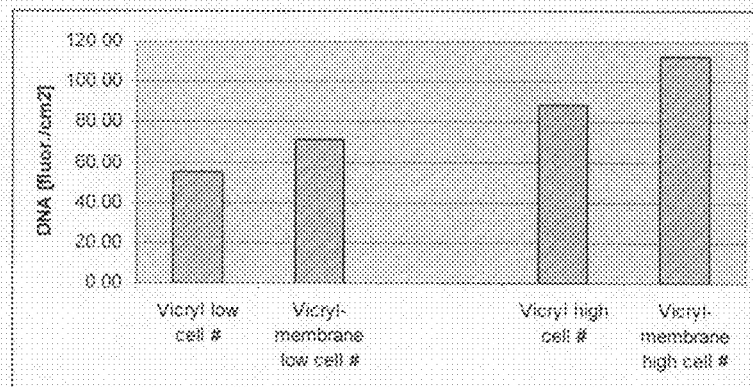
FIG. 5 shows cell adhesion to the scaffold system shown in FIG. 4.

DNA content of Vicryl control construct and Vicryl-membrane composite seeded with fibroblasts demonstrated the increased seeding density/efficiency of the membrane-composite construct (see, FIG. 5). At low and high cell density, DNA content was 30% higher than the scaffold-alone control.

EXAMPLE 4

In a further in vitro illustrative of the method according to the present disclosure, calf tendon fibroblasts were seeded onto scaffold-membrane composites. A commercially available knitted material, Vicryl®, was used as the scaffold. Pursuant to the present methods, 2 grams of solid PLGA was dissolved in 20 ml of acetone and the scaffold submerged in the solution. The solvent was evaporated leaving the scaffold embedded in solid PLGA material (See, FIG. 4). The scaffold-membrane composite was subsequently cut and stored under vacuum. Prior to seeding with cells, the composite was immersed in DMEM growth medium containing 10% bovine fetal calf serum, non-essential amino acids, L-glutamine and Penicillin-Streptomycin antibiotics.

Fibroblasts were isolated from bovine patellar tendon using enzymatic digestion. Cells were seeded in tissue culture plated and grown in the presence of DMEM growth medium containing fetal bovine serum, non-essential amino acids and antibiotics. Confluent cell cultures were harvested with Trypsin-EDTA solution; cells were collected by centrifugation and resuspended in growth medium. Subsequently, cells were seeded onto the scaffold-membrane composite. The cultures were placed in tissue culture incubators (37° C., 5% $CO_2$) for up to 21 days.

Cells attached to the scaffold-membrane composite, proliferated and deposited an extracellular matrix, filling the spaces between the scaffold fibers by day 16. Thus, as the sheet degraded, the cells were able to close the windows in the knitted scaffold.

EXAMPLE 5

In a further in vitro illustrative of the method according to the present disclosure, calf tendon fibroblasts were seeded onto scaffold-membrane composites. A commercially available knitted material, Vicryl®, was used as the scaffold. Pursuant to the present methods, 2 grams of solid PLGA was dissolved in 20 ml of acetone and the scaffold submerged in the solution. The solvent was evaporated leaving the scaffold embedded in solid PLGA material. The scaffold-membrane composite was subsequently cut and stored under vacuum. Prior to seeding with cells, the composite was immersed in DMEM growth medium containing 10% bovine fetal calf serum, non-essential amino acids, L-glutamine and Penicillin-Streptomycin antibiotics.

Fibroblasts were isolated from bovine patellar tendon using enzymatic digestion. Cells were seeded in tissue culture plated and grown in the presence of DMEM growth medium containing fetal bovine serum, non-essential amino acids and antibiotics. Confluent cell cultures were harvested with Trypsin-EDTA solution; cells were collected by centrifugation and resuspended in growth medium. Subsequently, cells were seeded onto the scaffold-membrane composite. The cultures were placed in tissue culture incubators (37° C., 5% $CO_2$) for up to 18 days. The tissue constructs were assessed by biochemical analysis.

To determine biochemical content of the constructs, the tissue constructs were digested with papain, and aliquots taken to determine the presence of glycosaminoglycans, collagen and DNA. The glycosaminoglycans were assessed by using the dye 1,9-dimethylmethylene blue, and the collagen was assessed by hydrolsis followed by determination of hydroxyproline, an amino acid characteristic of collagen. To determine the presence of cells and their metabolic activity, the digest was assayed for DNA content. Separate aliquots of the constructs assayed by XTT (Roche Molecular Biochemicals, Germany) to determine cell metabolic activity.

Biochemical analysis of the constructs showed the constructs contained cells, and XTT analysis showed that the cells were viable and metabolically active. The cells had successfully deposited collagen and glycosaminoglycan onto the scaffold-mesh composite material. The GAG concentration was 0.039 μg/ng DNA, and the collagen concentration was 0.02 μg/ng DNA. These results show that the tendon fibroblasts were able to attach to the scaffold-membrane composite, proliferate, and deposit onto the scaffold-membrane an extracellular matrix with components characteristic of connective tissue.

It will be understood that various modifications may be made to the embodiments disclosed herein. Therefore, the above description should not be construed as limiting, but merely as exemplifications of preferred embodiments.

What is claimed is:

1. A three-dimensional tissue comprising a biocompatible scaffold, a continuous membrane of bioabsorbable material encasing the scaffold, and extracellular matrix deposited directly by cells onto the scaffold, wherein the three-dimensional tissue comprises no living cells, wherein the bioabsorbable material is selected from at least one member of the group consisting of glycolide, lactide, trimethylene carbonate, dioxanone, caprolactone, alkylene oxides, ortho esters, polymers and copolymers therof, collagen, hyaluronic acids, alginates, and mixtures thereof.

2. A tissue according to claim 1, further comprising at least one therapeutic agent.

3. A tissue according to claim 2, wherein the therapeutic agent is selected from the group consisting of growth factors, cytokines, lipids, guidance factors, antimicrobial agents, and antibiotics.

4. A tissue according to claim 2, wherein the therapeutic agent is VEGF or FGF4.

5. A tissue scaffold system comprising a biocompatible scaffold and a pre-formed, continuous biocompatible membrane comprising a synthetic polymer, the biocompatible membrane having an engineered surface texture, and wherein the tissue scaffold system comprises no living cells and the synthetic polymer comprises a bioabsorbable material selected from at least one member of the group consisting of glycolide, lactide, trimethylene carbonate, dioxanone, caprolactone, alkylene oxides, ortho esters, polymers and copolymers thereof, collagen, hyaluronic acids, alginates, and mixtures thereof.

6. A tissue scaffold system according to claim 5, wherein the biocompatible scaffold comprises a three dimensional network.

7. A tissue scaffold system according to claim 6, wherein the three dimensional network comprises a mesh.

8. A tissue scaffold system according to claim 6, wherein the three dimensional network comprises a member selected from the group consisting of a non-woven felt and a sponge.

9. A tissue scaffold system according to claim 5, wherein the biocompatible membrane includes a surface having ridges.

10. A tissue scaffold system according to claim 5, wherein the biocompatible membrane includes a surface having grids.

11. A tissue scaffold system according to claim 5, wherein the biocompatible membrane includes a surface having an ionic charge.

12. A tissue scaffold system according to claim 5, wherein the biocompatible membrane includes a surface having a cell attachment ligand.

13. A tissue scaffold system according to claim 5, wherein the biocompatible scaffold comprises a bioabsorbable material.

14. A tissue scaffold system according to claim 5, wherein the biocompatible scaffold comprises a non-bioabsorbable material.

15. A tissue scaffold system according to claim 14, wherein the non-bioabsorbable material is selected from at least one member of the group consisting of polypropylene, polyethylene, polyamide, polyalkylene therephalate, polyvinylidene fluoride, polytetraflouroethylene and blends and copolymers thereof.

16. A tissue scaffold system according to claim 5, wherein the biocompatible membrane is bioabsorbable.

17. A tissue scaffold system according to claim 5, wherein the scaffold is embedded in the biocompatible membrane.

18. A tissue scaffold system according to claim 5, wherein the scaffold is enveloped by the biocompatible membrane.

19. A tissue scaffold system according to claim 5, wherein the biocompatible membrane is layered with the scaffold.

20. A tissue scaffold system according to claim 5, wherein the biocompatible membrane encases the biocompatible scaffold.

* * * * *